United States Patent [19]

Fujii et al.

[11] 4,252,902

[45] Feb. 24, 1981

[54] PROCESS FOR PURIFICATION OF CRUDE KALLIKREIN

[75] Inventors: Setsuro Fujii, Toyonaka; Kiyoaki Noda, Takarazuka; Akio Yokoshima, Ikeda, all of Japan

[73] Assignee: Toho Pharmaceutical Industries Co., Ltd., Osaka, Japan

[21] Appl. No.: 58,292

[22] Filed: Jul. 17, 1979

[30] Foreign Application Priority Data

Jul. 25, 1978 [JP] Japan ................... 53-91044

[51] Int. Cl.$^3$ .................... C12N 9/50; C12N 9/94
[52] U.S. Cl. ................... 435/186; 435/188; 435/213; 435/226; 435/815
[58] Field of Search ........... 435/186, 188, 212, 213, 435/219, 226, 803, 815; 424/110

[56] References Cited

U.S. PATENT DOCUMENTS

| | | | |
|---|---|---|---|
| 3,100,736 | 8/1963 | Werle et al. | 424/110 |
| 3,746,622 | 7/1973 | Nishikawa et al. | 435/213 |
| 3,912,595 | 10/1975 | Philipp et al. | 435/219 |
| 3,994,782 | 11/1976 | Tokuyasu et al. | 435/226 |
| 4,020,268 | 4/1977 | Nishikawa et al. | 435/815 |
| 4,064,010 | 12/1977 | Harris et al. | 435/803 |

FOREIGN PATENT DOCUMENTS 52-18883  2/1977  Japan ...................... 435/212

Primary Examiner—Peter A. Hruskoci
Attorney, Agent, or Firm—Berman, Aisenberg & Platt

[57] ABSTRACT

A process for purification of crude kallikrein utilizing a specific affinity of kallikrein to p-aminobenzamidine, which comprises bringing a solution, containing kallikrein and contaminated by other undesirable enzymes and proteins, into contact with a water-insoluble carrier combined with p-aminobenzamidine, exclusively eluting out the other enzymes and proteins from the carrier by the use of a buffer solution of lower NaCl concentration and then exclusively eluting out kallikrein by the use of a buffer solution of higher NaCl concentration.

7 Claims, No Drawings

PROCESS FOR PURIFICATION OF CRUDE KALLIKREIN

The invention relates to a process for the purification of kallikrein and, more particularly, to a simple and efficient process for the purification of crude kallikrein extracted from internal organs, particularly from pancreas, of mammals by the use of a specific reagent.

As is well known to those skilled in the art, kallikrein, a proteolytic enzyme, occurs in various internal mammal organs and liberates kinins from kininogen in blood plasma. Since kinin has potency as a vascular relaxant, kallikrein is effective as a capillary or coronary vasodilator and has been clinically used as a hypotensive agent.

Kallikrein is generally obtained by extraction from mammal pancreas, urine, submaxillary gland, blood and the like. However, since the extract is contaminated with various undesirable enzymes and proteins, it must be purified before it is administered as a medicine to avoid side effects due to undesirable contaminants.

Various methods for purifying crude kallikrein-containing extract (hereinafter referred to as "crude kallikrein") have heretofore been practiced, using for example, ion-exchange chromatography, gel filtration, salting out and affinity chromatography which employs a naturally occurring high molecular enzyme inhibitor. These conventional methods, however, require complicated procedures and complicated equipment and yet yield unsatisfactory results in purification-efficiency. Accordingly, such methods are not suitable for the purification of crude kallikrein on a large scale.

For example, the previously-mentioned affinity chromatography, which is considered the most effective, posesses various drawbacks in that the inhibitor required in this method is expensive, unstable, difficult to recover and of low selectivity.

It has now been found that kallikrein has a specific affinity to p-aminobenzamidine and that crude kallikrein can be purified in high efficiency by utilizing the affinity. The present invention is based on this finding.

Thus, the invention provides a process for the purification of crude kallikrein utilizing a specific affinity of kallikrein to p-aminobenzamidine, which comprises bringing the crude kallikrein into contact with a water-insoluble carrier combined with p-aminobenzamidine, exclusively eluting out other undesirable other enzymes and proteins from the carrier by the use of a buffer solution having lower NaCl concentration, and then exclusively eluting out kallikrein attached to the carrier by the use of a buffer solution having a higher NaCl concentration.

The process according to the invention is detailed below.

A water-insoluble carrier is set to combine with p-aminobenzamidine. For this purpose, it is preferred that a spacer, which is defined in the specification as a chemical mediator allowing the carrier to bind with p-aminobenzamidine, is first set to combine with a water-insoluble carrier. In this case, in order to facilitate the binding, the water-insoluble carrier is usually functionally-activated by a suitable reagent prior to a reaction with the spacer. The resultant product which has been linked with the spacer is then allowed to combine with p-aminobenzamidine in the presence of a reagent used for peptide-bond formation.

The water-insoluble carrier thus combined with p-aminobenzamidine is packed into a column, an aqueous solution of crude kallikrein is then poured into the column and elution is carried out using phosphate buffer containing sodium chloride. The buffer containing sodium chloride in a lower concentration, i.e., 0.05 to 0.2 M, usually 0.1 M NaCl is first employed as eluent, whereby undesirable enzymes and proteins, such as trypsin, chymotrypsin, kininase (which decomposes released kinin and thus degrades the substantial potency of kallikrein) and the like, are eluted out of the column, leaving kallikrein in the column. The kallikrein left in the column can be thoroughly eluted out of the column by the use of buffer containing sodium chloride in a higher concentration, usually 0.5 to 2.0 M NaCl, preferably 0.5 M NaCl. In this manner highly-purified kallikrein can be obtained.

A similar result can be obtained by adding the carrier combined with p-aminobenzamidine to crude kallikrein suspended in a buffer solution containing sodium chloride in a low concentration, stirring and then centrifuging the resultant mixture, and eluting the resultant precipitate with a buffer containing sodium chloride in a higher concentration.

The spacer used in the present invention may be a compound which contains at least two functional groups, i.e. a carboxyl group, and another functional group by which the compound can be bound to the water-insoluble carrier to be employed. Thus, when the carrier is activated by cyanogen bromide, aminocarboxylic acids, particularly $\epsilon$-aminocaproic acid, may be used as a spacer.

The water-insoluble carrier may be a compound which is substantially insoluble in water and yet contain hydrophilic groups. Said compound includes, among others, agarose and dextran.

The reaction between the spacer combined with the carrier and p-aminobenzamidine is carried out in the presence of a reagent useful for the formation of a peptide bond. Said reagent may be any one known to those skilled in the art, and 1-ethyl-3-(3'-dimethylaminopropyl)-carbodiimide is the most preferred.

The pH of the phosphate buffer used for the elution of kallikrein and also for the elution of undesirable enzymes and proteins must be below 7.4 in order to avoid protonation of an amide group originating from p-aminobenzamidine. The preferred pH of the phosphate buffer lies between 6.9 and 7.4. This phosphate buffer can be prepared according to a method described in literature, for example, "Method in Enzymology, No. 1", page 143, (1955) Academic Press, New York.

The water-insoluble carrier combined with p-aminobenzamidine can be repeatedly employed by washing the carrier once used with a phosphate buffer.

The following examples are provided to illustrate the present invention and are not intended to limit the present invention.

EXAMPLE 1

Preparation of agarose combined with p-aminobenzamidine (1) Activation of agarose by cyanogen bromide Four hundred ml of agarose (Cefarose-4B ®, Pharmacia Fine Chemicals Co. Ltd) is placed in a glass filter, filtered with suction, rinsed with 500 ml of distilled water and transferred into a beaker. The same volume of distilled water as of the pre-treated agarose is charged into the beaker while stirring. To the resultant suspension is added at one time a solution of 40 g of cyanogen bromide dissolved in 400 ml of distilled water while stirring by means of a magnetic stirrer.

The mixture is adjusted to pH 10.5 to 11.0 by adding 3.5 N NaOH and stirred for 15 minutes at 20° C. The reaction mixture is filtered, a solid portion is rinsed successively with 5 liters of distilled water and 5 liters of 0.1 N NaHCO$_3$ aqueous solution and suction-filtered.

(2) Preparation of agarose combined with ϵ-aminocaproic acid

A solution of 52.4 g of ϵ-aminocaproic acid dissolved in 400 ml of 0.1 M NaHCO$_3$ aqueous solution is adjusted to pH 9.5 by adding 1 N NaOH. The activated agarose obtained under (1) above is added to the solution and the mixture is stirred for 24 hours at 4° C. The reaction mixture is filtered with suction and washed successively first by the use of 5 liters of 0.1 M NaHCO$_3$ aqueous solution, 5 liters of 1 M NaCl aqueous solution and, finally, 5 liters of distilled water.

(3) Preparation of agarose combined with p-aminobenzamidine

Four hundred ml of agarose combined with ϵ-aminocaproic acid which has been obtained under (2) above is suspended in 400 ml of distilled water. To the resultant mixture is added a solution of 2.1 g of p-aminobenzamidine hydrochloride dissolved in 100 ml of distilled water while stirring, and pH of the mixture is adjusted to 4.5 by adding 1 N HCl. To the mixture, 23.8 g of 1-ethyl-3-(3-dimethylaminopropyl) carbodiimide dissolved in 40 ml of distilled water is added, and the resultant mixture is stirred for 24 hours at room temperature while keeping the mixture at pH 5 by adding 1 N HCl. The reaction mixture is filtered with suction and a solid portion is washed sequentially with 5 liters of 0.1 M acetic acid buffer solution of pH 4 (1 M NaCl) and 5 liters of 0.1 M tris hydrochloric acid buffer solution of pH 8 (1 M NaCl) and then filtered with suction to give 390 ml of agarose combined with p-aminobenzamidine.

EXAMPLE 2

Purification of crude kallikrein by column operation

Five grams of crude solid extract containing kallikrein derived from pig pancreas is suspended in 500 ml of 10 mM phosphate buffer (pH 7.4) and the suspension is stirred for 2 hours at 4° C. The supernatant solution obtained by centrifuging the suspension is rendered 80% saturation with ammonium sulfate and the mixture is stirred for 2 hours at 4° C. The mixture is allowed to stand at 0° C. for about 2 hours and centrifuged. The precipitate thus obtained is dissolved in a minimum amount of 50 mM phosphate buffer (pH 7.4) and the resultant solution is dialyzed against 50 mM phosphate buffer. NaCl is added to the dialyzed solution so that the concentration of NaCl may become 0.1 M. The resultant solution is subjected to the following purification process.

One hundred ml of agarose combined with p-aminobenzamidine is charged into a column and buffered at a pH of 7.4 by washing with 50 mM phosphate buffer at pH 7.4 (0.1 M NaCl). The dialyzed solution obtained above is poured into the column and eluted with about 500 ml of 50 mM phosphate buffer of pH 7.4 (0.1 M NaCl), whereby trypsin, chymotrypsin, kininase and undesirable proteins, all having a low affinity to p-aminobenzamidine, are eluted out. Successively, kallikrein is eluted out by using 500 ml of 50 mM phosphate buffer of pH 7.4 (0.5 M NaCl).

The fraction containing kallikrein is collected and dialyzed against distilled water and, then, lyophylized. The quality of thus obtained kallikrein (20 mg) is compared with that of the crude extract used as the starting material. The results are recorded in Table 1 which shows that the specific hypotensive activity of the purified kallikrein has been increased by a factor of 80 as compared with that of the starting material.

TABLE 1

|  | crude kallikrein | purified kallikrein |
|---|---|---|
| proteins (mg) | 2500 | 20 |
| hypotensive activity unit | 1250 | 800 |
| specific activity | 0.50 | 40.0 |
| BAEE* activity μmol/hr | 840000 | 41160 |
| ATEE** activity μmol/hr | 5400000 | 25088 |
| casein activity O.D. 750/hr | 297600 | 1064 |

*Benzoyl-L-arginine ethylester . HCl
**Acetyl-L-thyrosine ethylester . H$_2$O

The relative hypotensive activity of the purified kallikrein against other activities is calculated from Table 1. The results are shown in Table 2 which shows that hypotensive activity is fairly high as compared with other activities.

TABLE 2

| hypotensive activity | BAEE activity | ATEE activity | casein activity |
|---|---|---|---|
| 1.0 | 51.5 | 31.4 | 1.3 |

EXAMPLE 3

Purification of crude killikrein by batch operation

Five grams of crude solid extract from pig pancreas is suspended in 500 ml of 10 mM phosphate buffer (pH 7.4) and the suspension is kept stirring for 16 hours at 4° C. The supernatant solution obtained by centrifuging the suspension is rendered 80% saturation with ammonium sulfate and the mixture is stirred for one hour at 4° C. After the mixture is allowed to stand for 8 hours, the mixture is centrifuged and the resultant precipitate is dissolved in 300 ml of 50 mM phosphate buffer (pH 7.4) and then dialyzed against 50 mM phosphate buffer. NaCl is added to the dialyzed solution so that the concentration of NaCl can reach 0.1 M. To this solution is added 100 ml of agarose combined with p-aminobenzamidine and the mixture is stirred for 1 hour and centrifuged. To the resultant precipitate is added 500 ml of 50 mM phosphate buffer of pH 7.4 (0.5 M NaCl) and the mixture is stirred for one hour and then centrifuged. The supernatant thus obtained is dialyzed against distilled water and lyophylized. The quality of kallikrein thus purified is compared with that of crude kallikrein extract used as a starting material. The results are recorded in Table 3.

TABLE 3

|  | crude kalikrein | purified kallikrein |
|---|---|---|
| proteins (mg) | 2500 | 30 |
| hypotensive activity unit specific | 1250 | 600 |

TABLE 3-continued

|  | crude kalikrein | purified kallikrein |
|---|---|---|
| activity | 0.50 | 20.0 |
| BAEE activity μmol/hr | 840000 | 22530 |
| ATEE activity μmol/hr | 5400000 | 20010 |
| casein activity O.D.$_{750/hr}$ | 297600 | 2020 |

The relative hypotensive activity of the purified kallikrein against other activities is calculated from Table 3. The results are shown in Table 4 which shows that hypotensive activity is fairly high as compared with other activities.

TABLE 4

| hypotenisve activity | BAEE activity | ATEE activity | casein activity |
|---|---|---|---|
| 1.0 | 37.6 | 33.4 | 3.4 |

The characteristic figures shown in Tables 1 and 3 were determined according to the methods described below.

1. Hypotensive activity (Frey biological unit)

An adult dog weighing about 17 kg is anesthetized with pentobarbital sodium. A canula filled with an isotonic NaCl solution containing heparin (1000 μ/ml) is inserted into the femoral artery of the dog. A sample is administered to the dog through the canula and the blood-flow increasing activity of the sample is determined by a square wave electromagnetic rheometer. The test results of the sample is compared with a standard kallikrein furnished by Bayer AG.

2. BAEE and ATEE activity (Hydrolyzing activity of esters—Hesterin's Method)

Benzoyl-L-arginine ethylester hydrochloride (BAEE) or acetyl-L-thyrosine ethyl ester H$_2$O(ATEE), both presented by Tanpaku-Kenkyu-Shoreikai (Protein Research Foundation in Japan), is dissolved in 0.2 M tris-hydrochloric acid buffer solution (pH 8.0) so that the concentration of the ester may become 25 mM. To 0.4 ml of the BAEE or ATEE solution, 0.1 to 0.5 ml of a sample solution is added. To the resultant solution is added 0.2 M tris-hydrochloric acid buffer solution to make 1 ml of the total volume and the mixture is allowed to react for 30 minutes at 37° C. The reaction is terminated by adding to the solution 1.5 ml of the mixture consisting of 2 M hydroxylamine and 3.5 N NaOH aqueous solution in a proportion of 1:1. Twenty minutes after the termination of the reaction, 1 ml of 18% trichloroacetic acid and 1 ml of 4 N NCl are added to the solution and the mixture is centrifuged after 30 minutes after the addition. The resultant supernatant is filtered. To the filtrate is added 1 ml of 10% ferric chloride aqueous solution and the absorbancy of the solution is determined at 530 mμ.

The potency per 1 ml of the sample is represented by the following equation.

$$\text{Potency} = 10(\mu\text{mol}) \times \frac{O.D.^* \text{ of blank at 530m}\mu - O.D. \text{ of Sample at 530m}\mu}{O.D. \text{ of blank at 530 m}\mu}$$

*Optical Density

3. Hydrolyzing activity of casein

Four grams of Hammarsten casein is thoroughly admixed with 2 ml of 2 N NaOH solution in a mortar and the mixture is suspended in 100 ml of 50 mM phosphate buffer. The suspension is adjusted to pH 7.4 by adding 2 N HCl and kept stirring for 3 hours. The suspension is then centrifuged at 3000 rpm for 10 minutes. The resultant supernatant is used as a substrate in Matsumura's method (see The Journal of Biochemistry, vol. 57, page 402, 1965).

4. Quantitative determination of proteins

Proteins are determined according to the method of Lowry et al. (see The Journal of Biological Chemistry, vol. 193, page 265, 1951).

What is claimed is:

1. A process for purifying crude mammal-pancreas-derived kallikrein containing undesirable enzymes or proteins which comprises:
   (a) bringing a solution containing the kallikrein, other enzymes and proteins into contact with water-insoluble carrier,
   (b) eluting out the other enzymes and proteins from the carrier with buffer solution having a low NaCl concentration from 0.05 to 0.2 M and a pH below 7.4 and then
   (c) eluting out kallikrein from the carrier with buffer solution having a higher NaCl concentration and a pH below 7.4,
the water-insoluble carrier being one which is combined with p-aminobenzamidine.

2. A process according to claim 1, wherein the carrier is combined with p-aminobenzamidine via a spacer capable of being bound to both of the carrier and p-aminobenzamidine.

3. A process according to claim 2, wherein the spacer is ε-aminocaproic acid

4. A process according to any one of claims 2 and 3, wherein the carrier is agarose activated by cyanogen bromide.

5. A process according to claim 1, wherein the buffer solution is a phosphate buffer having a pH between 6.9 and 7.4.

6. A process according to claim 1 wherein the higher NaCl concentration is from 0.5 to 2.0 M.

7. A process according to claim 1 wherein the p-aminobenzamidine is chemically bound to the carrier.

* * * * *